United States Patent [19]

Fortin et al.

[11] Patent Number: 5,554,530
[45] Date of Patent: Sep. 10, 1996

[54] ASEPTIC IN VITRO ENDOMYCORRHIZAL SPORE MASS PRODUCTION

[75] Inventors: J. André Fortin, Neufchatel; Marc St-Arnaud, Laval; Chantal Hamel, St-Roch-de-l'Achigan; Claude Chavarie; Mario Jolicoeur, both of Montréal, all of Canada

[73] Assignee: Université de Montréal, Montreal, Canada

[21] Appl. No.: 286,116

[22] Filed: Aug. 4, 1994

Related U.S. Application Data

[63] Continuation-in-part of Ser. No. 102,950, Aug. 6, 1993, abandoned.

[51] Int. Cl.$^6$ .............................. C12N 1/14; C12N 1/04; A01H 15/00; A01H 17/00
[52] U.S. Cl. ..................... 435/256.8; 435/252.5; 435/254.1; 435/254.11; 435/911; 435/240.45; 435/240.46; 435/240.47; 435/240.48; 47/1.1
[58] Field of Search ....................... 435/252.5, 254.1, 435/254.11, 911, 240.45, 240.46, 240.47, 240.48, 284, 256.8; 47/1.1

[56] References Cited

U.S. PATENT DOCUMENTS

| | | | |
|---|---|---|---|
| 4,599,312 | 7/1986 | Rhone-Poulenc | 435/172.3 |
| 4,945,059 | 7/1990 | Okii et al. | 435/254.1 |
| 4,999,299 | 3/1991 | Shillito et al. | 435/240.47 |
| 5,096,481 | 3/1992 | Sylvia et al. | 71/65 |

FOREIGN PATENT DOCUMENTS

| | | |
|---|---|---|
| 0209627 | 1/1987 | European Pat. Off. . |

OTHER PUBLICATIONS

Bethlenfalvay, G. J., 1992, Amer. Soc. of Agr., Special Publication #54, Madison Wisc., pp. 1–27.
Linderman, R. G., 1992, Amer. Soc. of Agr., Special Publication #54, Madison Wisc., pp. 45–70.
Wood, T. et al., 1992, Mycoorhizae Functioning; an Integrative Plant–Fungal Process, pp. 468–487, Ed. M. F. Allen, Academic Press, N.Y..
Williams, G., 1992, Methods in Microbiology, vol. 24, 203–220, Ed. Norris, Read & Varma, Academic Press, London.
Jackson et al., 1972, Soil Sci. Soc. Amer. Proc., vol. 36, pp. 64–67.
Hall, I. R., 1979, Soil Biol. Biochem., vol. 11, pp. 85–86.
Mosse, 1975, Physiol. Plant Pathology, vol. 5, pp. 215–223.
Howeler et al., 1982, New Phytol., vol. 90, pp. 229–238.
Mosse et al., 1984, Can. J. Bot., vol. 62, pp. 1523–1530.
Tepfer, 1984, Cell, vol. 37, pp. 959–967.
Mugnier et al., 1987, Phytopathology, vol. 77, pp. 1045–1050.
Mosse, 1988, Can. J. Bot., vol. 66, pp. 2533–2540.
Fortin, J. A. et al., 1979, New Phytol., vol. 83, pp. 109–119.
Johnson et al., 1957, Plant & Soil, vol. 8, pp. 335–337.
Becard et al., 1988, New Phytol., vol. 108, pp. 211–218.
Tepfer et al., 1981, C. R. Acad. Sci., Paris III, vol. 292, pp. 153–156.
Chilton et al., 1982, Nature, vol. 295, pp. 432–434.
Anand, V. K., 1977, American Journal of Botany, vol. 64 (2), pp. 153–158.
Becard et al., 1989, New Phytol., vol. 112, pp. 77–83.
Hamill et al., 1987, Biotechnology, vol. 5, pp. 800–804.
Mugnier, 1988, Plant Cell Rep., vol. 7, pp. 9–12.
Parr et al., 1988, Plant Cell Rep., vol. 7, pp. 309–312.
Doner et al., Biotech. Techniques, 1991, vol. 5, No. 1 pp. 25–28.
Petit et al., 1983, Mol. Genet., vol. 190, pp. 204–14.
Gerdemann et al., 1963, Trans. Brit., Mycol. Soc., vol. 46, pp. 235–244.
Furlan, 1980, Trans. Brit. Mycol. Soc., vol. 75, pp. 336–338.

*Primary Examiner*—John W. Rollins
*Assistant Examiner*—Francisco C. Prats
*Attorney, Agent, or Firm*—Jacobson, Price, Holman & Stern, PLLC

[57] ABSTRACT

The present invention relates to a method of producing mycorrhizal fungal propagules in vitro in a two-compartment container having a gellified medium, which comprises the steps of: a) cultivating aseptically transformed dicotyledon root organs, capable of autonomous growth in vitro, in a first compartment containing a mineral minimal medium with sugar, wherein the medium is suitable for root growth; b) inoculating the transformed root organs with endomycorrhizal spores; and c) cultivating the inoculated transformed root organs for a time sufficient for the mycorrhizal fungi to transfer to a second root-free and root exudate-free compartment containing the mineral minimal medium of step a) and for the mass production of fungal propagules to occur in the second compartment.

18 Claims, 3 Drawing Sheets

ASEPTIC IN VITRO ENDOMYCORRHIZAL SPORE MASS PRODUCTION

RELATED APPLICATIONS

This application is a continuation-in-part of application Ser. No. 08/102,950 filed on Aug. 6, 1993, now abandoned.

BACKGROUND OF THE INVENTION (a) Field of the Invention

The invention relates to a method for the in vitro aseptic mass production of endomycorrhizal fungal propagules, mainly spores, using a transformed root or a root-hypocotyl explant cultivated in a two-compartment Petri dish or bioreactor.

(b) Description of Prior Art

Arbuscular mycorrhizal fungi (AM) are beneficial fungi in that they colonize the cells of feeding roots of plants and stimulate uptake of phosphorus from the soil. Hyphae of the fungus grow outwardly from the root, well beyond the phosphate depletion zone (the zone from which the available phosphate has already been consumed by the plant). Selected AM fungi have been shown to enhance the growth of numerous plants of economic importance (Bethlenfalvay, G. J., 1992, *Amer. Soc. of Agr.*, Special Publication #54, Madison Wis., pp. 1–27), including agronomic, horticultural and forest plant.

Furthermore, it has been observed that colonization by an endomycorrhizal fungus may protect the roots of the mycorrhized plant from pathogens in the soil (Linderman, R. G., 1992, *Amer. Soc. of Agr.*, Special Publication #54, Madison Wis. pp. 45–70).

However, despite the large amount of work carried out to date, the main difficulty in applying endomycorrhizae is that, it is not known how to produce their propagules in large quantities for commercial application (Wood, T. and B. Cummins, 1992, *Mycorrhizae Functioning; an Integrative Plant-Fungal Process*, pp. 468–487, Ed. M. F. Allen, Academic Press, New York). It is believed that no one has ever succeeded in cultivating them in a sterile medium without the host plant (Bécard, G. & Y. Piché, 1992, *Methods in Microbiology*, Vol. 24, 90–108, Ed. Norris, Read & Varma, Academic Press, London).

Unlike most symbiotic micro-organisms which are parasitic or saprophytic, AM fungi are obligate biotrophs which have so far resisted all attempts to be cultivated axenically (in pure culture); (Williams, G., 1992, *Methods in Microbiology*, Vol. 24, 203–220. Ed. Norris, Read & Varma, Academic Press, London). This lack of independent growth has not prevented vesicular-arbuscular mycorrhizal fungi from becoming distributed world-wide as a symbiotic partner of most vascular plants, under a wide variety of pedologic and climatic conditions (Bethlenfalvay, G. J., 1992, *Amer. Soc. of Agr.*, Special Publication #54, Madison Wis., pp. 1–29).

The large number of attempts at mycorrhization which have been carried out so far have consisted of using inoculums prepared from complete plants which are cultivated in pots or a greenhouse. Inoculation is nearly always carried out with specially gathered mycorrhizal roots, or sometimes with a suspension of spores, Jackson et al. (Jackson et al, 1972, *Soil Sci. Soc. Amer. Proc.*, Vol. 36, 64–67) used lyophilized roots, while Hall (Hall I. R., 1979, *Soil Biol. Biochem.*, Vol. 11, 85–86), recommends using soil pellets mixed with infected roots.

In all cases, one of the problems encountered is the possibility of introducing contaminants into the soil through inoculation of the endomycorrhizal fungi, particularly when for reasons of plant health it is necessary to disinfect the soil before planting, thereby resulting in destruction of the endomycorrhizal fungi naturally present. Moreover, the time required to produce an inoculum is generally two-four months, which is long enough to produce many contaminants. Such problems have hindered commercialization of the inoculums. In addition, the inoculums cost at least as much as, or more than, the fertilizers which would be required to obtain the same yield. Consequently the large scale use of endomycorrhizal fungi has not yet been adopted in agricultural practice due to the problems of producing an inoculum in large amounts, free of contaminants, yet easy to store and easy to handle on the land (Wood, T. and B. Cummins, 1992, *Mycorrhizae Functioning: an Integrative Plant-Fungal Process*, pp. 468–487, Ed. M. F. Allen, Academic Press, New York).

Cultivation of vesicular-arbuscular mycorrhizal fungi under axenic conditions (i.e. without a host plant) continues to be a preoccupation and represents one of the most challenging goals of modern plant biology. Using roots growing in vitro as plant partners, Mosse provided new scientific insights on this question when they succeeded in establishing arbuscular mycorrhizal symbiosis in vitro (1975, *Physiol. Plant Pathology*, Vol. 5, 215–223). However, colonization and sporulation were limited in these monoxenic systems. The VAM have also been established in solution culture (Howeler et al, 1982, *New Phytol.*, Vol. 90, 229–238; Mosse et al, 1984, *Can. J. Bot.*, Vol. 62, 1523–1530).

For example, Mosse reported approximately 50% colonization of *Zea mays* roots after nine weeks in a nutrient film system. The inoculum produced in their nutrient system, however, was primarily colonized root material. In general, sporulation in solution culture systems has been poor. This is due to the fact that VA-mycorrhiza are inhibited by excessive moisture and poor aeration in the natural environment.

In recent years, culture of isolated roots was given a new impetus with the use of roots genetically transformed by the Ri plasmid of *Agrobacterium rhizogenes* (Tepfer, 1984, *Cell*, Vol. 37, 959–967). Rapid growth of axenic "hairy roots" led Mugnier and Mosse (1987, *Phytopathology*, Vol. 77, 1045–1050) to inoculate such roots with vesicular-arbuscular mycorrhizal fungi. They observed some vesicular-arbuscular mycorrhizal colonization on transformed roots of *Convolvulus sepium* inoculated with germinated spores of *Glomus mosseae*. Some evidence of limited independent growth of *G. Intraradices* was also observed (Mosse, 1988, *Can. J. Bot.*, Vol. 66, 2533–2540). These authors thus demonstrated that root organ cultures have potential for growing vesicular-arbuscular mycorrhizal fungi in vitro. The method used, however, did not result in the reproducible generation of the entire life-cycle of the fungus including the production of viable spores nor the ongoing cultivation of the symbiotic root-organ system.

Further, Mugnier and Mosse (1987, *Phytopathology*, Vol. 77, 1045–1050) do not teach a method for the co-culture of the symbiotic combination of the root and the endomycorrhizal fungi and wherein the endomycorrhizal fungi has the opportunity to grow into a root-free compartment to produce the endomycorrhizal spores in mass quantity.

Mugnier et al., in U.S. Pat. No. 4,599,312 issued on Jul. 8, 1986 in the name of Rhone-Poulenc Agrochimie, discloses a method of obtaining endomycorrhiza formation with vesicles and arbuscules in vitro. The method comprises producing dicotyledone roots which have been genetically transformed by inserting genes of root inducing or tumor inducing plasmids into the genome of dicotyledone roots, and then inoculating the cultivated converted roots with pregerminated endomycorrhizal spores. Mugnier et al. discloses the preparation of these converted roots inoculated with endomycorrhizal spores divided in three steps: 1) conversion of the root; 2) cultivation of the converted root; and 3) spore germination and mycorrhization.

They do not disclose the in vitro sporulation of the endomycorrhizal fungi nor the ongoing cultivation of the symbiotic root-organ system. Moreover, no provision is made to create a root-free and root exudate-free compartment for promoting massive sporulation.

Sylvia et al., in U.S. Pat. No. 5,096,481 issued on Mar. 17, 1992 in the name of University of Florida, discloses a vesicular-arbuscular mycorrhizal inoculum composition comprising a host plant roots colonized by at least one species of vesicular-arbuscular mycorrhizal fungus. The colonized roots having a particle size in the range of 33 μm to about 425 μm and a propagule density of about 10,000 to about 1,000,000 vesicular-arbuscular mycorrhizal fungi propagules per gram dry mass of host plant root comprise an effective plant growth enhancing agent which is advantageously and efficiently stored, transported and applied in agricultural methods. It has been discovered that subjecting the colonized roots to methods of size reduction such as a high shear size reduction process in liquid, causes the reduction of the size of the roots while actually increasing the fungi propagule density thereof. This method is not aseptic and allows for contamination to occur.

Wood et al., in European Patent Application No. EP-A-209,627 published on Jan. 28, 1987, teaches a process for the production of mycorrhizal fungi in association with plant root organ culture comprising establishing root cultures and inoculating the established root culture with endomycorrhizal spores. In this method no provision is made to built a barrier preventing root exudates to reach for the extramatrical phase; without such a barrier the numbers of spores produced in the vicinity of the root remains very small and not industrially feasible. However, the amount of spores obtained in the best conditions is in the order of 83±32 spores for 30 ml of medium, which is a minute amount, and Wood et al. mention (page 17, line 24) that 1.7 spores/ml medium are obtained. It would thus be highly desirable to be provided with a method which would allow for the production of 6000–7000 spores/ml medium which are aseptic and readily recovered.

Okii et al., in U.S. Pat. No. 4,945,059 issued on Jul. 31, 1990, disclose a method of producing endomycorrhizal fungal spores using potato roots and a porous amphoteric ion exchanger. However, this process is not aseptic and only allows for minute quantities of spores produced. Here again, no provision is made to create the barrier to root diffusates of the present invention.

There is not disclosed a method for the aseptic in vitro mass production of endomycorrhizal fungal spores.

It would be highly desirable to be provided with a method for the in vitro mass production of arbuscular endomycorrhizal fungal propagules, mainly spores, which would be, contamination-free, simple, inexpensive and effective.

SUMMARY OF THE INVENTION

One aim of the present invention is to provide a method for in vitro mass production of endomycorrhizal fungal propagules, mainly spores.

Another aim of the present invention is to provide for a method for the in vitro aseptic mass production of endomycorrhizal fungal propagules, mainly spores, which would be, contamination-free, simple, inexpensive and effective.

Another aim of the present invention is to provide for the ongoing cultivation of the AM symbiotic root organ system.

A further aim of the present invention is to provide for conditions that will promote AM spore production.

In accordance with the present invention, there is provided an aseptic in vitro method of mass production of endomycorrhizal spores.

The present invention give unexpected results in view of the prior art, in that no one skilled in the art could have imagine that to allow for the isolation of the endomycorrhizal fungi would dramatically promote sporulation and would allow mass production of the fungal spores. It was thought that the root was essential for the growth of the symbiosis and for the sporulation. Surprisingly, it was discovered in accordance with the present invention, that a simple physical barrier in the dish used for the co-culture of the inoculated root, which delimit a root-free and root exudate-free compartment, would increase the occurrence of sporulation tremendously. It is believed that this is mainly due to the fact that the root uses the fungi for its own benefit and would not allow the fungi to reproduce itself, probably by producing sporulation-inhibiting substances in its surrounding medium. Thus, it is believed that the fungi would have to, in nature, get as far away from the root as possible in order for sporulation to occur, yet keeping a link via its mycelium to obtain the energy from the root. The method of the present invention is totally innovative and based on this new theory, and reproduce, by using the physical barrier, the nature requirement for the fungi sporulation to occur.

In accordance with the present invention there is provided a method of producing mycorrhizal fungal spores in vitro in a two-compartment container having a gellified medium, which comprises: a) cultivating aseptically transformed dicotyledon root organs, capable of autonomous growth in vitro, in a first compartment containing a mineral minimal medium with sugar, wherein the medium is suitable for root growth; b) inoculating the transformed root organs with endomycorrhizal spores selected from the group consisting of *Glomus intraradices, Glomus aggregatum, Glomus versiforme, Scutellospora heterogama, Glomus etunicatum, Glomus mosseae, Glomus lamellosum, Glomus macrocarpum, Gigaspora margarita, Sclerocystis sp.* ; c) cultivating the inoculated transformed root organs for a time sufficient for the mycorrhizal fungi to grow into a second root-free and root exudate-free compartment containing a mineral minimal medium without sugar and for production of fungal spores to occur in the second compartment; and d) recovering the produced fungal spores of step c) from the second root-free compartment gellified medium.

In accordance with the present invention, the term gellified medium is intended to mean a solidified medium such as agar or gellan, among others.

The root organs of the present invention are capable of autonomous growth without hormone addition by including a piece of hypocotyl or by genetical transformation of the root, The root organs of the present invention are dicotyledon root organs including a part of the hypocotyl to form root-hypocotyl explants or are dicotyledon roots transformed with a bacterium containing a root-inducing plasmid or a tumor-inducing plasmid.

The root organs of the present invention are dicotyledon root organs selected from the group consisting of *Daucus carota, Datura stramonium, Lycopersicon esculentum, Lycopersicon pimpinellifolium, Medicago sativa, Physalis exocarpa, Solanum melanocerasum, Tagetes patula, Tagetes erecta* and *Trifolium pratense.*

The endomycorrhizal spores of the present invention are selected from the group consisting of *Glomus intraradices, Glomus aggregatum, Scutellospora heterogama, Glomus etunicatum, Glomus versiforme, Glomus mosseae, Glomus lamellosum, Glomus macrocarpum, Gigaspora margarita, Sclerocystis sp.*

In accordance with the present invention there is also provided a method of producing mycorrhizal fungal spores in vitro in a compartmentalized bioreactor having a plurality of root-free and root exudate-free compartments having a gellified medium for mycorrhizal fungi growth, which comprises the steps of: a) cultivating aseptically transformed dicotyledon root organs, capable of autonomous growth in vitro, in a compartmentalized bioreactor having a plurality of solid support elements having a root-contacting surface comprising a mineral minimal medium with sugar, wherein the medium is suitable for root growth, defining root compartments wherein solid support elements in proximity of a root but not having a root-contacting surface defining a plurality of root-free and root exudate-free gellified compartments for mycorrhizal fungi growth and sporulation; b) inoculating the transformed root organs of step a) with endomycorrhizal spores selected from the group consisting of *Glomus intraradices, Glomus aggregatum, Glomus versiforme, Scutellospora heterogama, Glomus etunicatum, Glomus mosseae, Glomus lamellosum, Glomus macrocarpum, Gigaspora margarita, Sclerocystis sp.*; c) cultivating the inoculated transformed root organs of step b) for a time sufficient for the mycorrhizal fungi to grow into a root-free and root exudate-free compartment for the production of fungal spores to occur in the root-free compartment; and d) recovering the produced fungal spores of step c) from the root-free and root exudate-free compartment gellified medium.

BRIEF DESCRIPTION OF THE DRAWINGS

Having thus generally described the nature of the invention, reference will now be made to the accompanying drawings, showing by way of illustration a preferred embodiment thereof, and wherein.

DETAILED DESCRIPTION OF THE INVENTION

It will be recognized by those skilled in the art that a large number of host plants can be employed for colonization of the VAM fungi. Exemplary of such plants are *Daucus carota, Lycopersicon esculentum* and *Trifolium pratense.* Roots 1-Root-Hypocotyl Explants The root-hypocotyl explants may be used in accordance with the present invention as in vitro autonomously growing root organs. The root-hypocotyl explants are prepared according to the following general procedure as described by Fortin J. A. et al. (1979, *New Phytol.*, vol. 83, 109–119).

In Fortin et al., the necessary conditions for sustained growth of *Pinus strobus* L. root systems from root-hypocotyl explants for use in the study of ectomycorrhizae are defined. Much attention was given to sterilization of seeds, cultivation of seedlings before excision, and composition of organic medium in respect of vitamins and growth factors, auxin, cytokinin, inositol and sucrose concentration. The longevity of the root systems under these conditions was assessed and the need for a piece of hypocotyl to be present was re-examined. Finally root systems grown under improved culture conditions were inoculated and successfully formed ectomycorrhizae.

Seeds of *P. strobus* were agitated in sterilized water for 2 h before being sterilized by immersion in 30% $H_2O_2$ for 15 min. The seeds were then washed for 10 min in each of three sterile water baths using magnetic stirrers. Germination took place at room temperature (21° C.) under diffused daylight on 0–05% agar medium, containing 5 $gl^{-1}$ of glucose, previously autoclaved for 15 min at 121° C. Five seeds at a time were germinated in each 11 cm Petri dish containing 15 ml of the medium adjusted to pH 6.5.

After 8 to 10 days, each uncontaminated and germinated seed was placed in a sterile 20×150 mm test tube stopped with a styrofoam plus and containing 15 $cm^3$ of vermiculite (sieved free of dust<1 mm), and 12 ml of a mineral solution containing in 1000 ml of distilled water 106 mg of $Ca(NO_3)_2.4H_2O$, 31 mg of $KH_2PO_4$, 55 mg of $MgSO_4.7H_2O$, 9 mg of $(NH_4)_2SO_4$, 1 ml of 1% ferric citrate in a 1% citric acid solution and 1 ml of the following trace element solution as defined by Johnson et al. (1957, *Plant & Soil*, Vol. 8, 337–353) containing in 1000 ml of distilled water, 3728 g of KCl, 1.546 g of $H_3BO_3$, 0.845 g of $MnSO_4.H_2O$, 0.575 g of $ZnSO_4.7H_2O$, 0.125 g of $CuSO_4.5H_2O$, and 0.018 g of $(NH_4)_6Mo_7O_{24}.4H_2O$. No attempt was made to adjust the pH of the solution in vermiculite since it is strongly buffered at pH 6.5.

Seedling development took place in a growth chamber under 15 klx, with 13 h of light at 26° C. alternating with 11 h of darkness at 21° C. for 30±1 days.

Two different media were prepared: an organic medium to be contained in a glass shell vial and a mineral medium to be contained in a glass Petri dish with vermiculite. The organic medium was composed of 1.0% agar with variable quantities of sucrose, vitamins, with or without plant hormones according to the experiment. The final pH of agar in the vials varied from 5.2 to 5.5 from one experiment to another. To prepare the organic medium, empty 12×35 mm shell vials were placed in deep 10×8 cm Petri dishes and autoclaved. The medium was separately autoclaved at the same time, in a 250 ml Erlenmeyer flask and later poured into the vials with a sterilized 50 ml syringe up to 2 mm from the brim. Quick cooling at 4° C. was necessary to prevent agar sedimentation in the vials. The mineral medium was composed as follows: 1000 ml of distilled water, 72 mg of $CaNO_3.4H_2O$, 20 mg of $MgSO_4.7H_2O$, 10 mg $KH_2PO_4$, 1 ml of a 1% ferric citrate solution in 1% citric acid solution, and 1 ml of the trace element solution described above. In 10×1.5 cm Petri dishes, 60 $cm^3$ of sieved vermiculite were moistened with 35 ml of this mineral solution. The plates were wrapped individually in paper towels and autoclaved for 20 min at 121° C. The paper towel was useful in removing condensed water after autoclaving.

To excise the root-hypocotyl explants, each seedling was removed from the tube and placed in a sterile 10×1.5 cm plastic Petri dish. The hypocotyl was cut with a sharp scalpel, first at 10 mm above the collar zone and then at 35 mm from this point down the root. By this means the meristem was eliminated and the formation of lateral roots was promoted. The explants were then rapidly transferred into sterile dishes containing a vial of the organic medium and the vermiculite moistened with the standard mineral medium. Finally, the entire length (10 mm) of the hypocotyl segment was pushed with a tweezer into the agar of the vial. Each dish was then wrapped in Saran plastic film to prevent evaporation and incubated in the dark at 21° C. for 6 weeks, unless otherwise stated. By this arrangement the hypocotyl of the explant was fed with the organic medium and the roots with the inorganic medium.

Replacement of Hormones by the Hypocotyls

Figures 1, 4A, 4B:
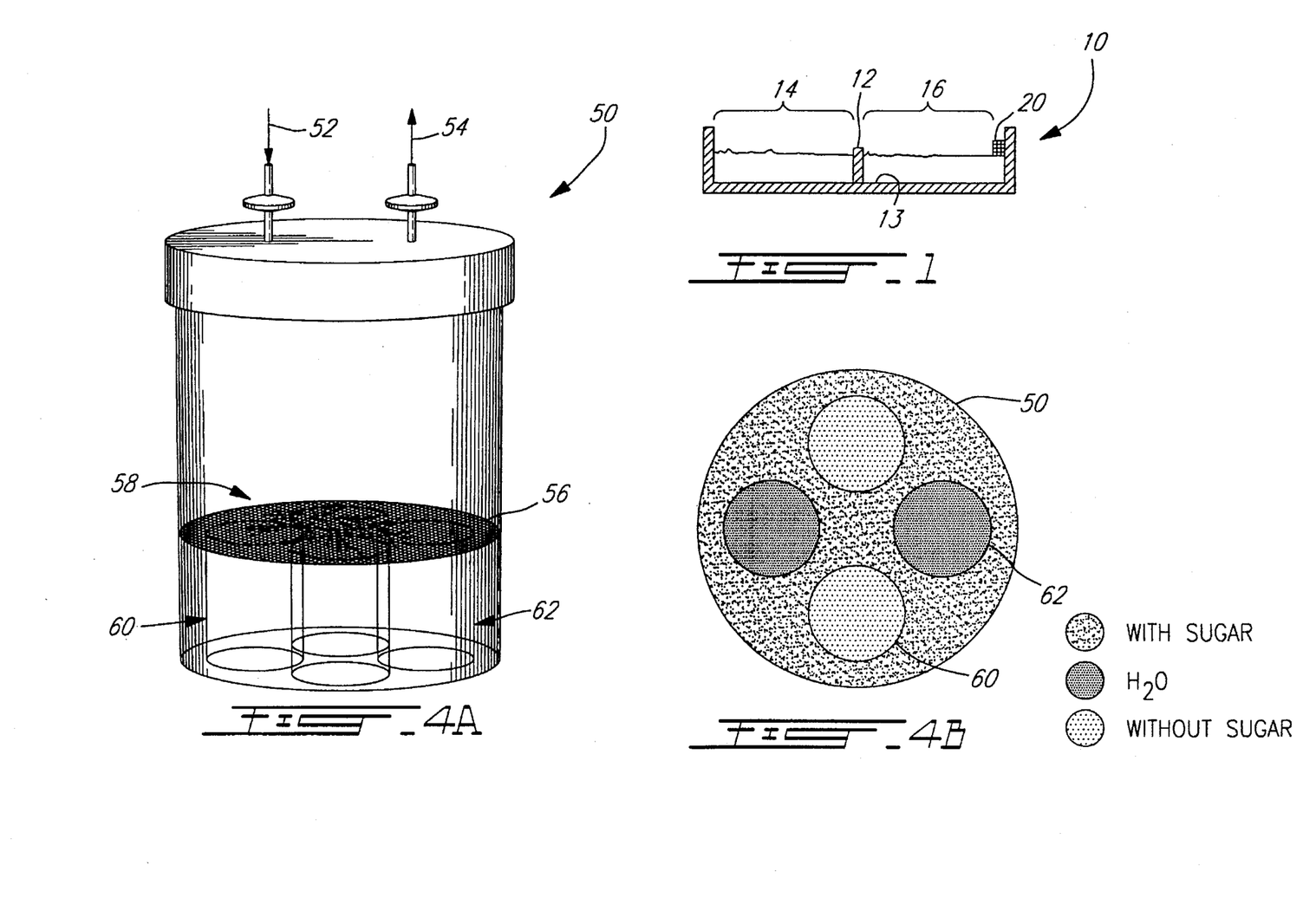
FIG. 1 is a cross-sectional view of a two-compartment Petri dish in accordance with the present invention.
FIG. 4A is a side view in accordance with another embodiment of the present invention.
FIG. 4B a top elevation view of an opened bioreactor of FIG. 4A.

Experiments were performed using explant with and without a part of the hypocotyl. In presence of hypocotyl and without hormonal addition root growth was 27.5 mm. Under the same set of conditions explants without hypocotyl and without hormones grew only 4.7 mm. The addition of napthalene acetic acid (NAA) to the hypocotyl free explant improved the growth but never to the same level of the explants with hypocotyl. This principle was applied to AM host plant using the same conditions as Bécard & Fortin (1988, *New Phytol.*, Vol. 108, 211–218). Root-hypocotyl explants demonstrated autonomous growth, in the absence of hormones, in a manner similar to the genetically transformed roots. Such roots were successfully inoculated with *Glomus intraradices, Glomus aggregatum, Glomus versiforme* and *Glomus mosseae*, and produced large number of vesicular-arbuscular mycorrhizal spores and mycelium, in the distal root and root exudate-free compartment (FIG. 1).

2- Transformed Roots

The bacterium *A. rhizogenes* is a soil-borne pathogen causing "hairy root" disease in dicotyledonous plant. When wounded tissues are infected with the bacteria, they form large numbers of roots (hairy roots) in 2–3 weeks. In a system analogous to crown gall tumors induced by the much studied *A. tumefaciens*, hairy roots synthesize opines (Tepfer and Tempé, 1981, *C.R. Acad. Sci. Paris III*, Vol. 292, 153–156). Their constitutive cells have integrated copies of T-DNA (Transfer DNA) which occurs in a large plasmid of *A. rhizogenes*, the Ri (Root-inducing) plasmid (Chilton et al., 1982, *Nature*, Vol. 295, 432–434).

Conversion of the root can take place as spelled out in the foregoing by transferring genes of Ri plasmid from Agrobacterium rhizogenes into the genome of the root organ. The culture medium for the bacterium *Agrobacterium rhizogenes* for the bacterium carrying the inducing plasmid may be of any appropriate known type, such as the medium Sucrose, Nutrient Broth, Yeast Extract (Anand V. K., 1977, *American Journal Of Botany*, Vol. 64 (2), 153–158).

The genes of the root-inducing plasmid may be provided in several ways, either directly by the bacterium *Agrobacterium rhizogenes*, a virulent plasmid carrier, or indirectly by a bacteria to which the root-inducing plasmid has been transferred by conjugation or to which T-DNA has been transferred by conversion.

The genes of the tumor inducing plasmid may equally be provided in several ways, either directly by the bacterium *Agrobacterium tumefaciens*, a virulent carrier of the plasmid, or indirectly by a bacterium to which the tumor inducing plasmid has been transferred, for example by conjugation, or to which T-DNA has been transferred by conversion.

After emerging from the infected tissue, the transformed roots can be subcultured as excised roots. On solid culture media, the fast-growing root apices can be freed of the original bacterial inoculum by the use of antibiotics such as carbenicillin or ampicillin. After several transfers without detectable contamination, a clonal culture, derived from a single root, is established. An example of production of such a clonally transformed root culture, established from carrot tissues, was described by Bécard and Piché (1989, *New Phytol.*, Vol. 112, 77–83) and in U.S. Pat. No. 4,599,312, the teachings of which is hereby incorporated by reference.

Various culture media may be used for growing such Ri T-DNA transformed roots: Murashige and Skoog (MS) medium or Gamborg B5 medium (Hamill et al., 1987, *Biotechnology*, Vol. 5, 800–804; Mugnier, 1988, *Plant Cell Rep.*, Vol. 7, 9–12); Parr et al., 1988, *Plant Cell Rep.*, Vol. 7, 309–312); and finally a modified White's medium (Bécard and Piché, 1989, *New Phytol.*, Vol. 112, 77–83). The last medium was preferred to MS, even when diluted, because it allowed significantly better growth of the roots. Specifically, the presence of ammonium in MS caused a rapid (less than two weeks) drop in the pH of the culture medium which was detrimental to the root growth. On White's medium, nitrogen exclusively in the form of nitrate is assimilated, which counteracts the acidification of the culture medium following root growth. In this way, the culture medium is buffered and is maintained at pH 6 for several months.

Fungal Inocula

Inoculation can be performed initially with surface sterilized spores (Bécard & Fortin, 1988, *New Phytol.*, Vol. 108, 211–218) and thereafter with spores aseptically produced on root organ culture.

Different forms of inocula may be used to form vesicular-arbuscular mycorrhiza with root-hypocotyl organ cultures or transformed root organ cultures: sporocarpic chlamydospores of *Glomus mosseae*, nonsporocarpic azygospores of *Gigaspora margarita* and chlamydospores of *Glomus intraradices, Glomus aggregatum* or *Glomus versiforme*. Virtually any kind of vesicular-arbuscular mycorrhizal fungus may provide propagules amenable to in vitro propagation.

The preferred fungus employed to colonize the roots may be selected from the group consisting of Glomus, Gigaspora, Entrophospora and Sclerocystis.

Dual Culture

Dual culture of root and fungus are established on solid media in a two-compartment Petri dish or in a liquid culture in a compartmentalized bioreactor.

1- Petri Dish Culture

The Petri dish is divided in two compartments, one for the co-culture of the symbiotic endomycorrhizal system permitting the formation of the intra-matrical phase, referred to as the proximal or intra-matrical phase compartment, and one for the proliferation of the AM fungal extra-matrical phase, referred to as the distal or extra-matrical phase compartment.

The distal or extra-matrical phase compartment must be so arranged that the medium will remain root-free and root exudate-free.

The culture medium of the proximal compartment consists of a mineral salt medium including sugars. The culture medium of the distal compartment is the same but sugars are omitted.

More specifically, the medium is that of Bécard & Fortin (1988, *New Phytol.*, Vol. 108, 211–218).

The sugars which may be used are selected from the group consisting of monosaccharide such as glucose or disaccharides, preferably sucrose.

The two-compartment Petri dish, in accordance with the present invention, is illustrated in FIG. 1 and is generally denoted 10, and the separation between the two compartment is a physical barrier 12 upwardly extending from the Petri dish inner bottom surface 13, defining two compartments 14 and 16. The dicotyledon root is aseptically cultivated in the proximal compartment 14. The root is then inoculated with a VAM fungus to obtain a symbiotic mycorrhizal root organ or better a segment of already established AM symbiotic system is transferred and the barrier 12 allows for the root and its released chemical compounds in culture to remain with the proximal compartment 14. This compartmentation of the root and its chemicals gives unexpected and surprising results, since once the extra-matrical phase of the endomycorrhizal fungus outgrows into the distal compartment 16, the endomycorrhizal fungus highly proliferates whereby extremely high level of sporulation are obtained. Limited fungal growth and much smaller number of spores are produced in the proximal compartment 14.

The preferred gellified medium used in accordance with the present invention is a gellan referred to as Gel-Gro™ (sold by ICN Biomedicals Canada Ltd., St-Laurent, Québec), which allows for an excellent growth of the root. Standard agar can also be successfully used in accordance with the present invention.

The sporulation compartment 16 may also be provided with a $CO_2$ source 20 located opposite to the physical barrier 12 which attract the mycorrhizal fungus and facilitate its transfer into the sporulation compartment 16. Such a $CO_2$ source 20 may be selected from calcium carbonate, magnesium carbonate or any other slow release $CO_2$ source.

The ideal root and VAM fungus symbiotic root organ which may be used in accordance with the present invention is selected from *Daucus carota* X *Glomus mosseae*; *Daucus carota* X *Glomus versiforme*; *Daucus carota* X *Glomus intraradices*; *Daucus carota* X *Glomus aggregatum*; *Trifolium pratense* X *Glomus intraradices*; *Trifolium pratense* X *Glomus aggregatum*.

2- Bioreactor Culture

The culture of transformed roots may be carried out industrially in a bioreactor. When a bioreactor is used, growth takes place very rapidly, but the culture medium must be properly aerated in order to avoid anoxia of the roots. Cultivation in a bioreactor is performed advantageously at ambient temperature (e.g. 20°–30° C.).

Figures 2A, 2B, 2C:
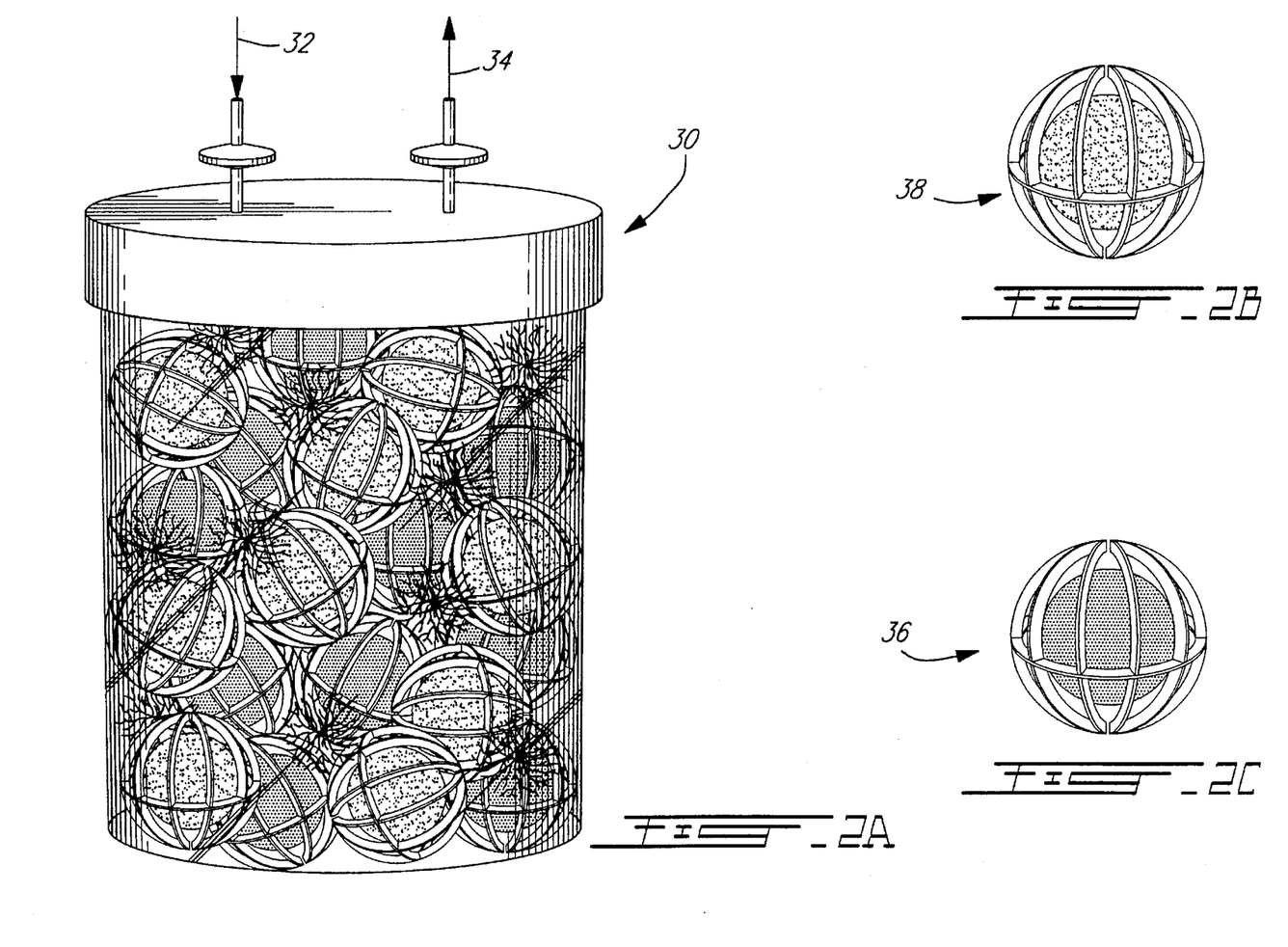
FIG. 2 is a side view of a bioreactor in accordance with one embodiment of the present invention.

The compartmentalized bioreactor in accordance with one embodiment of the present invention is illustrated in FIG. 2 and is generally denoted 30, with a gas entry 32 for the entry of gases such as air with 2% $CO_2$ and a gas exit 34. The bioreactor contains an alternating alignment of solid support elements 36 containing a mineral medium with carbon source (sugar) in a gel and solid support elements 38 containing a mineral medium without a carbon source (without sugar) in a gel. All solid support elements are open structures.

The bioreactor 30 as illustrated in FIG. 2 is operated without agitation and under aerated conditions.

The culture medium of the solid support elements 36 with carbon source (sugar) consists of a mineral salt medium including carbon source (sugar), more specifically, the medium is the minimal medium described in Table I below, preferably with 1% sucrose.

The culture medium of the solid support elements 38 without a carbon source (without sugar) consists of a mineral salt medium lacking a carbon source (no sugar), more specifically, the medium is the minimal medium described in Table I below.

The inoculation of the transformed roots or of the root-hypocotyl organ is effected simultaneously with the filling of the solid support elements 36 and 38.

The ideal root and VAM fungus symbiosis couple which may be used in accordance with this embodiment of the present invention is selected from *Daucus carota* X *Glomus mosseae*; *Daucus carota* X *Glomus versiforme*; *Daucus carota* X *Glomus intraradices*; *Daucus carota* X *Glomus aggregatum*, *Trifolium pratense* X *Glomus intraradices* and *Trifolium pratense* X *Glomus aggregatum*.

Figures 3A, 3B, 3C:
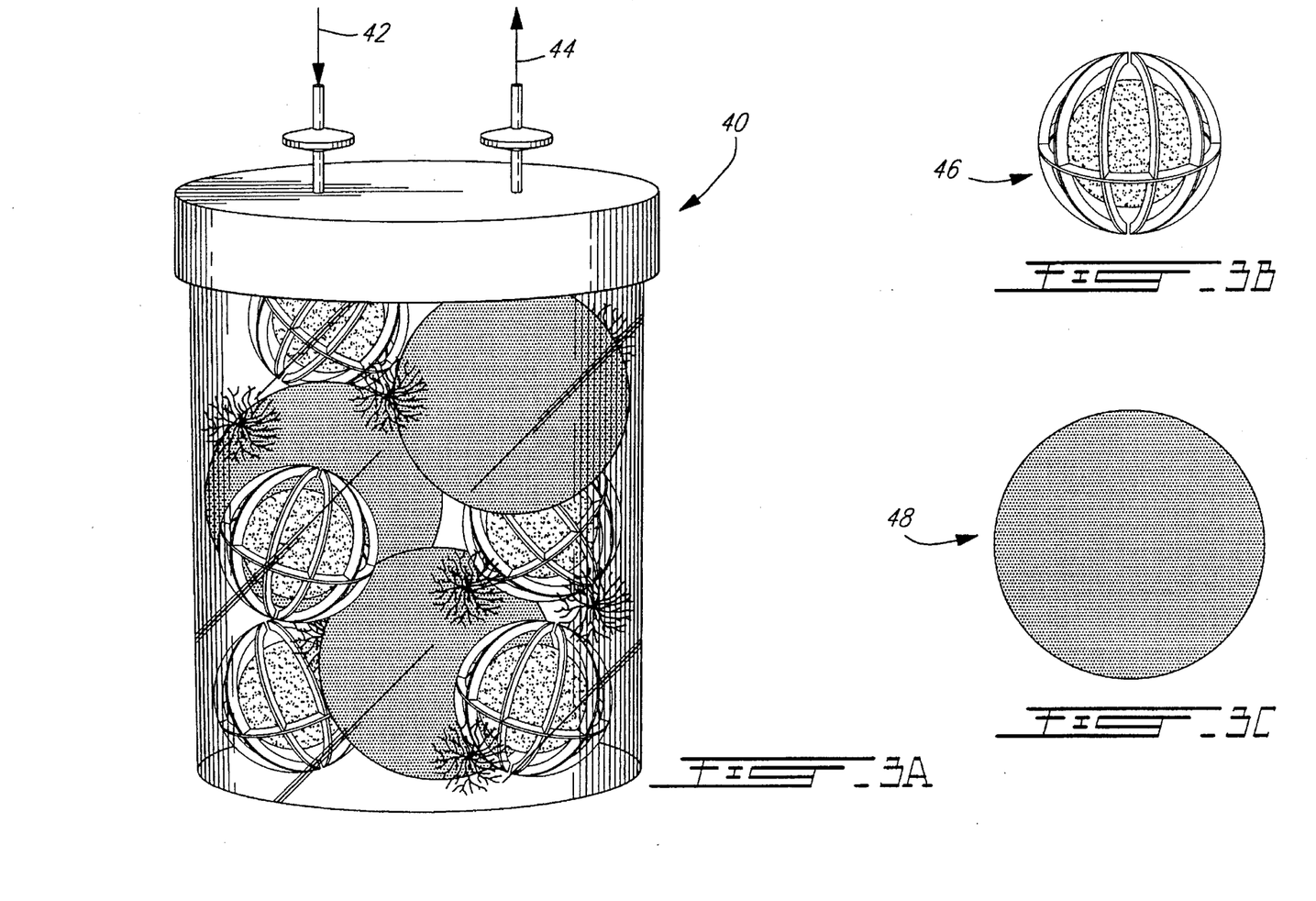
FIG. 3 is a side view of a bioreactor in accordance with another embodiment of the present invention.

The compartmentalized bioreactor in accordance with another embodiment of the present invention is illustrated in FIG. 3 and is generally denoted 40, with a gas entry 42 for the entry of gazes such as air with 2% $CO_2$ and a gas exit 44. The bioreactor 40 contains an alternating alignment of solid support elements 46 containing a mineral medium with a carbon source in a gellan or agar and solid support elements 48 containing a mineral medium without a carbon source in a gellan or agar. The solid support elements 46 are open structures whereas the solid support elements 48 are closed structures that can minimize root passage and limit diffusion of root exudates. Both solid support elements 46 and 48 can contain the same minimal medium with a carbon source.

The bioreactor 40 as illustrated in FIG. 3 is operated without agitation and under aerated conditions.

The culture medium of the solid support elements 46 consists of a mineral salt medium including a carbon source, more specifically, the minimal medium described in Table I below, preferably with 1% sucrose.

The culture medium of the solid support elements 48 consists of a mineral salt medium lacking sugars and vitamins, more specifically, the medium is the minimal medium described in Table I below.

The inoculation of the transformed roots or the root-hypocotyl organ culture is effected simultaneously with the filling of the solid support elements 46 and 48.

The ideal root and VAM fungus symbiosis couple which may be used in accordance with this embodiment of the present invention is selected from *Daucus carota* X *Glomus mosseae*; *Daucus carota* X *Glomus versiforme*; *Daucus carota* X *Glomus intraradices*; *Daucus carota* X *Glomus aggregatum*, *Trifolium pratense* X *Glomus intraradices* and *Trifolium pratense* X *Glomus aggregatum*.

The compartmentalized bioreactor in accordance with another embodiment of the present invention is illustrated in FIGS. 4A and 4B and is generally denoted 50, with a gas entry 52 for the entry of gazes such as air with 2% $CO_2$ and a gas exit 54. The bioreactor 50 contains a perforated sheet 56 horizontally extending and located near the bottom of the bioreactor 50 filled with a liquid culture medium including a carbon source. The perforations on the sheet 56 are of diameter which allows for the passage of the VAM fungi and not for the passage of the root itself.

The transformed roots or the root hypocotyl organs 58 rest on the perforated sheet 56. Under the sheet 56 are a plurality of alternating containers 60 and 62. The containers 60 contain a mineral medium without sugar and the containers 62 contain $H_2O$.

The bioreactor 50 as illustrated in FIGS. 4A and 4B is operated without agitation and under aerated conditions.

The culture medium of the bioreactor 50 consists of a mineral salt medium including sugars, more specifically, the medium is the minimal medium described in Table I below, preferably with 1% sucrose.

The culture medium of the containers 60 consists of a mineral salt medium lacking sugars and vitamins, more specifically, the medium is the minimal medium described in Table I below.

The inoculation of the transformed roots or the root-hypocotyl organ culture is effected by placing the roots 58 on the sheet 56.

The ideal root and VAM fungus symbiosis couple which may be used in accordance with this embodiment of the present invention is selected from *Daucus carota* X *Glomus intraradices*; *Daucus carota* X *Glomus aggregatum*, *Trifolium pratense* X *Glomus intraradices* and *Trifolium pratense* X *Glomus aggregatum*.

Spore Recovery

1- Petri Dish Culture

Once the VAM spores are produced in the sporulation compartment, they are recovered according to the following procedure.

The gel is subjected to a chelation solubilization under mild conditions by exposure to either 10 mM sodium citrate buffer (pH 6.0) or to 1 mM sodium hexametaphosphate (pH 6.6) as described by Landis W. Doner et al. (*Biotech. Techniques*, 1991, Vol. 5, No. 1, 25–28).

2- Bioreactor Culture

Once the VAM spores are produced in the bioreactors illustrated in FIGS. 2 and 3, they are recovered according to the following procedure.

The gel is subjected to a chelation solubilization under mild conditions by exposure to either 10 mM sodium citrate buffer (pH 6.0) or to 1 mM sodium hexametaphosphate (pH 6.6) as described by Landis W. Doner et al. (*Biotech. Techniques*, 1991, Vol. 5, No. 1, 25–28).

Once the VAM spores are produced in the bioreactor illustrated in FIGS. 4A and 4B, they are recovered from the roots and the liquid culture medium is collected.

The present invention will be more readily understood by referring to the following examples which are given to illustrate the invention rather than to limit its scope.

EXAMPLE I

Production of VAM Fungi Sporulation in a Two-Compartment Petri Dish Using a Transformed Root VAM fungi spores were produced in a two-compartment Petri dish as illustrated in FIG. 1 using the host plant/VAM fungi symbiotic model of *Daucus carota* transformed roots and *Glomus intraradices*.

1. Transformed Root Organ Cultures:

1.1 Bacterial Strains

Three strains of *Agrobacterium rhizogenes* were used in the transformation of roots. These include the agropine types $A_4$ and R100 and a non-identified type $A_{2/83}$ (Dr. Brian Ellis, University of Guelph, Ontario. Bacterial suspensions were prepared by inoculating 5 ml of nutrient broth (Difco, Detroit, Mich.) with a loopful of *Agrobacterium rhizogenes* and incubating at 24° C. for 48 hours on a rotary shaker (100 rpm).

1.2 Plant Material

Plant material of *Daucus carota* was obtained from seed under aseptic conditions. The seeds were surface sterilized by immersion in ethanol (90%) for 2 min then $H_2O_2$ (30%) for 10 min. The seeds were rinsed three times for five minutes each with sterile distilled $H_2O$ and transferred onto PCA (Potato Dextrose Agar, Sigma Chemical Co., St. Louis, Mo.) to test for the presence of contaminants. Germination was carried out in the dark at room temperature. The sterile seedlings were transferred onto Murashige and Skoog (MS, 1% Difco Bacto-agar) medium for inoculation with *Agrobacterium rhizogenes*.

1.3 Induction of Transformed Roots

Using a syringe, the *Agrobacterium rhizogenes* suspension was delivered into the hypocotyl of the seedling. The seedlings were incubated at 21° C. Roots emerged from the inoculated site within 2 to 4 weeks. These roots were excised and cultured onto Murashige and Skoog medium (1% Difco Bacto-agar) supplemented with carbenicillin (500 mg/L) to eliminate further Agrobacterial growth. The roots were subcultured weekly on the aforementioned media until they were freed of the original bacterial inoculum. The resulting clonal cultures of transformed roots are continuously maintained by subculturing onto fresh modified White's media every 3 to 4 weeks. Plant hosts other than *Daucus Carota* may require continuous culturing on Murashige and Skoog medium.

1.4 Confirmation of Root Transformation

The cultured roots were analyzed using the ammoniacal silver nitrate method described by Petit et al. (1983, *Mol. Genet.*, Vol. 190, 204–214). This technique allows for the detection of opines which are characteristically synthesized in transformed tissue into a root-free and root exudate-free compartment.

2. VAM Fungal Material:

Spores of *Glomus intraradices* were obtained from a pot culture supplied by Centre de Recherches Premier Ltée., Rivière-du-Loup, Québec (DAOM 197198, deposited at the Biosystematic Research Center, Ottawa, Ontario, Canada). Spores were harvested from the pot culture using the wet sieving technique of Gerdemann and Nicolson (1963, *Trans. Brit. Mycol. Soc.*, Vol. 46, 235–244) and further purified through the density gradient centrifugation technique described by Furlan (1980, *Trans. Brit. Mycol. Soc.*, Vol. 75, 336–338). The isolated spores were surface sterilized by two chloramine T (2%) washings followed by 5 washings with an antibiotic solution of 1% streptomycin and 0.5% gentamycin. The surface sterilized spores were deposited onto water agar and incubated at 4° C. until needed.

3. Establishment and Subculture of Dual Cultures

Dual cultures consisting of *Daucus carota* root organ material and *Glomus intraradices* VAM fungal material were initiated by subculturing transformed root apices onto minimal media. Surface sterilized spores were deposited in the proximity of the root apices. The ensuing colonization of the root was accomplished within 4 weeks. These primary mycorrhizal dual cultures can easily be propagated and maintained by subculturing colonized root apices onto fresh minimal media. This allows for the continuous cultivation of VAM fungi symbiotic root organ cultures.

4. Composition of Culture Medium

Transformed roots were cultured on modified White's media (or Murashige and Skoog media) supplemented with sucrose (3.0%) and solidified with GEL-GRO gellan gum™ (0.2%; ICN Biomedicals Canada Ltd., St-Laurent, Québec). The pH was adjusted to 5.5. Mycorrhizal transformed roots were cultured on minimal media supplemented with sucrose (1.0%) and solidified with GEL-GRO gellan gum (0.4%). The media used are all described in Table I below.

TABLE I

| | MEDIUM | | |
|---|---|---|---|
| | MODIFIED WHITE'S (mg/L) | MINIMAL (mg/L) | MURASHIGE AND SKOOG (mg/L) |
| $MgSO_4 \cdot 7H_2O$ | 731 | 731 | 370 |
| NaCl | 96 | — | — |
| $KNO_3$ | 80 | 80 | 1900 |
| KCl | 65 | 65 | — |
| $NaH_2PO_4 \cdot 2H_2O$ | 21.5 | — | — |
| $KH_2PO_4$ | — | 4.8 | 170 |
| $Ca(NO_3)_2 \cdot 4H_2O$ | 288 | 288 | — |
| Sucrose | 30,000 | 10,000 | 30,000 |
| NaFeEDTA | 8 | 8 | 43 |

TABLE I-continued

| | MEDIUM | | |
|---|---|---|---|
| | MODIFIED WHITE'S (mg/L) | MINIMAL (mg/L) | MURASHIGE AND SKOOG (mg/L) |
| KI | 0.75 | 0.75 | 0.83 |
| $MnCl_2.4H_2O$ | 6 | 6 | — |
| $ZnSO_4.7H_2O$ | 2.65 | 2.65 | 8.6 |
| $H_3BO_3$ | 1.5 | 1.5 | 6.2 |
| $CuSO_4.5H_2O$ | 0.13 | 0.13 | 0.025 |
| $Na_2MO_4.2H_2O$ | 0.0024 | 0.0024 | 0.25 |
| Glycine | 3 | 3 | — |
| Thyamine hydrochloride | 0.1 | 0.1 | 0.1 |
| Pyridonine hydrochloride | 0.1 | 0.1 | 0.5 |
| Nicotinic acid | 0.5 | 0.5 | 0.5 |
| Myo inositol | 50 | 50 | 100 |
| GEL-GRO gellangum | 4,000 | 2,000 | 4,000 |

5. Establishment of Dual Cultures in Two-Compartment Petri Dishes

The Petri dish was prepared such that the proximal compartment contained 20 ml of minimal media with sugar and the distal compartment contained 7 ml of minimal media without sugar. The movement of hyphae from the proximal and distal compartments was facilitated by constructing a minimal media bridge in the distal compartment which joins the media in the compartment to the top of the dividing barrier.

The cultures were initiated by subculturing a block of gelose containing colonized root apices from the dual culture collection into the proximal compartment. Any roots which grew into the distal compartment during the culture period were excised in order to ensure that this compartment remained root-free and root exudate-free. A calcium carbonate, in powdered form, was placed in the distal compartment. This resulted in the release of $CO_2$ which stimulates and attracts hyphae towards the distal compartment. Within 4 to 6 weeks the hyphae emerged from the inoculum and grew into the root-free and root exudate-free distal compartment where a dramatic increase in sporulation was observed.

6. Recovery of Spores

The spores were harvested from the two-compartment Petri dish by liquefying the medium. This was achieved by cutting the spore-containing gelose into small cubes and placing them into a 30° C. solution of sodium citrate buffer (10 mM, pH of 6.0). The solution was stirred until all the solid cubes were liquefied. The spores were then recovered by filtration. The method of recovery has been shown to have no negative effect on the viability of fungi.

7. Results

The movement of hyphae from the proximal compartment into the distal compartment may occur in as little as one week. The use of a $CO_2$ source plays a key role in reducing the time required for hyphae to grow into the distal compartment. In an experiment conducted with the model *Daucus carota* and *Glomus intraradices*, a production of 30,000 spores was observed within a 6 week period in the distal compartment, whereas this number in the proximal compartment with root and root exudate produced at the most 3,000 spores.

EXAMPLE II

Production of YAM Fungi Sporulation in a Two-Compartment Petri Dish Using a Root-Hypocotyl Explant VAM fungi spores were produced in a two-compartment Petri dish as illustrated in FIG. 1 using the host plant/VAM fungi symbiotic model of *Trifolium pratense* root-hypocotyl explant and *Glomus intraradices*.

1. Root-Hypocotyl Explant Cultures
1.1 Plant Material

The plant material of *Trifolium pratense* was obtained from seed under aseptic conditions. The seeds were surface sterilized by immersion in ethanol (90%) for 2 min and $H_2O_2$ (30%) for 10 min. The seeds were rinsed three times for five minutes each with sterile distilled $H_2O$ and transferred onto PDA (Potato Dextrose Agar, Sigma Chemical Co., St. Louis, Mo.) to test for the presence of contaminants. Germination was carried out in the dark at room temperature. The sterile seedlings were transferred onto modified White's medium and incubated at 21° C. for 5 to 7 days.

The root-hypocotyl cultures were initiated by excising the shoot of each seedling such that approximately 2 cm of hypocotyl remained attached to the root system. These explants were maintained on modified White's medium and incubated in the dark at 26° C.

2. VAM Fungal Material

This procedure is as described in section 2. of Example I.

3. Composition of Culture Medium

The root-hypocotyl explants of *Trifolium pratense* were initiated on modified White's media supplemented with sucrose (3.0%) and solidified with GEL-GRO gellan gum (0.2%). The pH was adjusted to 5.5. The colonization of the root-hypocotyl explants of *Trifolium pratense* by *Glomus intraradices* was effected on minimal media supplemented with sucrose (1.0%) and solidified with GEL-GRO gellan gum (0.1%). The media used are as described in Table I above.

4. Establishment of Dual Cultures in Two-Compartment Petri Dishes

The Petri-dish is prepared such that the proximal compartment contains 20 ml of minimal media with sugar and the distal compartment contains 7 ml minimal media without sugar. The movement of hyphae from the proximal compartment to the distal compartment is facilitated by constructing a minimal media bridge in the distal compartment which joins the media in the compartment to the top of the dividing barrier.

The dual cultures consisting of *Trifolium pratense* root-hypocotyl explants and *Glomus intraradices* VAM fungal material were initiated by transferring the root-hypocotyl explant from the modified White's medium culture onto compartment I. The explant was inoculated with three blocks of gelose containing approximately 30 *Glomus intraradices* spores each. The cultures were incubated in the dark at 26° C. Any roots which grew into compartment II during the culture period were excised in order to ensure that this compartment remained root-free. Within 4 weeks the root-hypocotyl explant was colonized by the inoculum. An additional 2 to 4 weeks was required before hyphae grew into compartment II and produced large quantities of spores.

5. Recovery of Spores

The spores were harvested form two-compartment Petri dish by liquefying the medium. The methodology is described in section 6 of Example I.

6. Results

Root-hypocotyl explants represent a host plant which is capable of growing autonomously without hormone addition. The process by which non transformed root organs are cultured is therefore facilitated as growth hormones are no longer required in the preparation of the cultures. Non transformed roots of endomycorrhizal host plants are colonized in the same manner as their transformed counterparts. Therefore, the results obtained when using dual cultures of *Trifolium pratense* root-hypocotyl explants and *Glomus intraradices* in the two-compartment Petri dish system are similar to those of their transformed counterparts in two-compartment Petri dishes.

EXAMPLE III

Production of VAM Fungi Sporulation in a Two-Compartment Petri Dish Compared to a One-Compartment Petri Dish VAM fungal spores were produced in a two-compartment Petri dish as illustrated in FIG. 1 using the host plant/VAM fungi symbiotic model of *Daucus carota* transformed roots and *Glomus intraradices*. VAM fungi spores were produced in a one-compartment Petri dish using the host plant/VAM fungi symbiotic model of *Daucus carota* transformed roots and *Glomus intraradices*. The spore production of the two systems are compared.

1. Transformed Root Organ Cultures

The bacterial strains, plant material, induction of transformed roots and confirmation of root transformation are as described in Example I sections 1.1 to 1.4.

2. VAM Fungal Material

This procedure is as described in section 2 of Example I.

3. Establishment and Subculture of Dual Cultures

This procedure is as described in section 3 of Example I.

4. Composition of Culture Medium

This procedure is as described in section 4 of Example I.

5. Establishment of Dual Cultures 5.1 Two-Compartment Petri dishes

The Petri dish was prepared such that the proximal compartment contained 20 ml of minimal media with sugar and the distal compartment contained 7 ml of minimal media without sugar. The movement of hyphae from the proximal compartment to the distal compartment was facilitated by constructing a minimal media bridge in the distal compartment which joins the media in the compartment to the top of the dividing barrier.

The cultures were initiated by subculturing a block of gelose containing colonized root apices from the dual culture collection into the proximal compartment. Any roots which grew into the distal compartment during the culture period were excised in order to ensure that this compartment remained root-free and root exudate-free. A source of $CO_2$, Calcium carbonate in powdered form, was placed in the distal compartment. This resulted in the release of $CO_2$ which stimulated and attracted hyphae towards the distal compartment. Within 4 to 6 weeks the hyphae had emerged from the inoculum and grown into the distal compartment where a dramatic increase in sporulation was observed.

5.2 One-Compartment Petri Dishes

The cultures were initiated by subculturing a block of gelose containing colonized root apices from the dual culture collection onto minimal media. The continued colonization of the newly produced roots was not hindered and therefore occurs on the entire surface of the Petri dish. Sporulation of *Glomus intraradices* within such one-compartment Petri plate occurred within 4 to 6 weeks.

6. Recovery of Spores

This procedure is a described in section 6 of Example I.

7. Results

In the two-compartment system using the models *Daucus carota* and *Glomus intraradices*, a potential production of 40,000 spores was observed within a 6 week period in an area of 28.37 mm. When the same model was cultured in a one-compartment system, 5,000 spores were produced in an area of 56.74 mm. Hence, in the two-compartment Petri dish system, spore production was 8 times greater in half the area. By way of extrapolation, the two-compartment system represents a potential spore production 16 times greater than attainable in the one-compartment Petri dish system.

EXAMPLE IV

Production of VAM Fungi Sporulation in a Bioreactor Using a Transformed Root Cultures of VAM infected transformed roots were conducted in a 1 L compartmentalized bioreactor configuration as illustrated in FIG. 2 and using a total of twelve (12) solid support elements.

1. Transformed Root

The roots of *Trifolium pratense* were transformed by the *Agrobacterium rhizogenes* bacteria as described in Example I.

2. Fungal Inoculation

Original *Trifolium pratense* infections with VAM *Glomus aggregatum* were done by the procedure as described in Example I. Subsequent subculturing for inocula preparation occurred by the transfer of 0.5 to 1.0 g of weight of fresh colonized roots to a Petri dish containing 20 ml of fresh solid mineral minimal media as described in Example I.

3. Bioreactor Preparation and Sterilization

The bioreactor consists of 1 L autoclavable polycarbonate jar (Nalgene company). Air filters of 0.2 μm pore size were used for filtering the inlet and outlet gas.

The solid support elements consist of a spherical structure that can hold gelified media and were non-restrictive to root contact or propagation. The solid support elements structure used are polypropylene TRI-PACKS™ 1½ beads (FABCO PLASTICS company) these structures elements prevent media contact between adjacent solid support elements.

The bioreactor was steam sterilized in an autoclave at 121° C. for 30 min. The solid support elements were sterilized separately from the bioreactor; six of the solid support elements were sterilized immersed within the mineral minimal medium with 1% sucrose and supplemented with 0.4% weight/volume of Gel-Gro™ as a gelifier in an autoclave at 121° C. for 35 min. The other six solid support elements were sterilized immersed within the mineral minimal medium without sugar and supplemented with 4% weight/volume of Gel-Gro™ as a gelifier in an autoclave at 121° C. for 35 min. Once sterilized and gelified, the mineral minimal medium, with and without 1% sugar, in excess at the periphery of the solid support elements was removed.

4. Bioreactor Inoculation

The colonized roots of *Trifolium pratense* with *Glomus aggregatum* are cultured on solid minimal mineral medium in Petri dish were used as inoculum.

The placement in the bioreactor of the colonized roots and the solid support elements was done simultaneously. The solid support elements containing the solidified media with and without sugar were placed alternatively to get the colonized roots in contact with the two different media.

5. Culture Parameters

Temperature: 24° C.

Inoculum: 3.7 g fresh weight of VAM *Glomus aggregatum* colonized roots of *Trifolium pratense*;

Volume of mineral media: 35 mL per solid support element
Aeration: 0.01 standard liter per minute (SLM) of a 2% $CO_2$ enriched air
Culture time in bioreactor: 8 weeks 6. Spore Recovery The harvested roots were transferred in liquid minimal mineral media with sugar in Petri dishes and then observed under microscope and subculture. The gelified media entrapped into the solid support elements were separately transferred into Petri dishes and then observed.

7. Results

After a month of culture 36,000 VAM spores was produced and a total of 120,000 VAM spores was obtained within the bioreactor after two months. The use of a carbon source free media reduced the presence of root growth in the solid support elements.

The colonized roots harvested showed regular growth with subsequent subculturing.

EXAMPLE V

Culture of VAM colonized transformed roots were effected in a 1 L compartmentalized bioreactor configuration as illustrated in FIG. 3 and using a total of ten solid support elements.

1. Transformed Root

The roots of Trifolium pratense were transformed by the *Agrobacterium rhizogenes* bacteria as described in Example I.

2. Fungal Inoculation

Original *Trifolium pratense* infections with VAM *Glomus aggregatum* were done as described in Example I. Subsequent subculturing for inocula preparation occurred by the transfer of 0.5 to 1.0 g fresh weight of colonized roots in a Petri dish containing 20 mL of fresh solid minimal mineral media described in Example I.

3. Bioreactor Preparation and Sterilization

Bioreactor consisted of a 1 L autoclavable polycarbonate jar (Nalgene Company). Air filters of 0.2 µm pore size were used for filtering the inlet and outlet gas.

Seven of the solid support elements consisted of a spherical structure that can hold the gelified media and were non-restrictive to the roots contact or propagation. The solid support elements structure polypropylene TRI-PACKS 1½ beads (Fabco Plastics Company) avoid any media contact between adjacent solid support elements. The other three solid support elements of a diameter of 2 inches were also spherical but made of a 250 µm pore size stainless steel grid which prevent root passage.

Bioreactor was steam sterilized in an autoclave (121° C. for 30 min). The solid support elements were sterilized separately from the bioreactor. The seven polypropylene beads were sterilized immersed within the mineral minimal media with 1% sucrose and supplemented with 0.4% weight/volume GEL-GRO gellan gum as gelifier in an autoclave (121° C. for 35 min) and the stainless steel beads (three) were sterilized immersed within the mineral minimal media without sugar and supplemented with 0.4% weight/volume GEL-GRO gellan gum as gelifier in an autoclave (121° C. for 35 min). Once sterilized and gelified, the mineral minimal media with and without sugar in excess at the periphery of the solid support elements was removed.

4. Bioreactor Inoculation

Colonized roots of *Trifolium pratense* with *Glomus aggregatum* cultured on solid minimal mineral media in Petri dishes were used as inoculum.

The placement in the bioreactor of the colonized roots and the solid support elements was done simultaneously. The solid support elements containing the solidified media with and without sugar were placed alternatively to get the colonized roots in contact with the two different mineral media.

5. Culture Parameters

Temperature: 24° C.
Inoculum: 7.6 g fresh weight of VAM *Glomus aggregatum* colonized roots of *Trifolium pratense*
Volume of mineral media: 35 mL per solid support element
Aeration: 0.01 standard liter per minute (SLM) of a 2% $CO_2$ enriched air
Culture time in bioreactor: 2 weeks 6. Spores Recovery The harvested roots were transferred in liquid minimal mineral media with sugar in Petri dishes and then observed under microscope and subculture. The gelified media entrapped into the solid support elements were separately transferred into Petri dishes and then observed.

7. Results

A total of 1,000 spores was obtained within the bioreactor.

The colonized roots harvested showed regular growth with subsequent subculturing

EXAMPLE VI

Culture of VAM infected transformed roots were effected in a 1 L compartmentalized bioreactor configuration as illustrated in FIG. 4.

1. Transformed Root

The roots of *Daucus carota* were transformed by the *Agrobacterium rhizogenes* bacteria as described in Example I.

2. Fungal Inoculation

Original *Daucus carota* infection with VAM *Glomus intraradices* were done by the same method described in Example I. Subsequent subculturing for inocula preparation occurred by the transfer of 0.5 to 1.0 g fresh weight of colonized roots in a Petri dish containing 20 ml of fresh liquid mineral minimal media as described in Example I.

3. Bioreactor Preparation and Sterilization

Bioreactor consisted of a 1 L autoclavable polycarbonate jar (Nalgene Company) with four glass ended tubes fixed at the bottom of the bioreactor and used as different mineral media containers. A 250 µm grid was placed at the top of all the containers. Air filters of 0.2 µm pore size were used for filtering the inlet and outlet gas.

Bioreactor was steam sterilized in an autoclave at 121° C. for 30 min. The different liquid mineral media used were sterilized separately from the bioreactor. Once sterilized, two containers were filled with demineralized water and two with the mineral liquid media without sugar. Surrounding volume was filled with liquid mineral media with 1% sucrose. All the liquid media levels were the same, right above the container top end. The use of the grid gave minimal roots contacts with the liquid media.

4. Bioreactor Inoculation

Colonized roots of *Daucus carota* with *Glomus intraradices* cultured on liquid minimal mineral media in Petri dishes were used as inoculum.

The colonized roots were placed to maximize the contact with different mineral media.

5. Culture Parameters

Temperature: 24° C.
Inoculum: 9.8 g fresh weight of VAM *Glomus intraradices* colonized roots of *Daucus carota*
Volume of mineral media: 35 mL per compartment and 100 mL for liquid mineral minimal with sugar Aeration: 0.01 standard liter per minute (SLM) of a 2% $CO_2$ enriched air Culture time in bioreactor: 9 weeks.

6. Spore recovery

The roots were harvested separately from the liquid mineral media over which they were growing and transferred in liquid minimal mineral media with sugar in Petri dishes and then observed under microscope and subcultured.

7. Results

A total of 14,300 spores was obtained within the bioreactor. The root wet weight did not increase. The spores were formed in the different media with a greater hyphal development in the $H_2O$ and minimal media without carbon source.

The colonized roots harvested showed regular growth with subsequent subculturing.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method of producing endomycorrhizal fungal spores in vitro in a two-compartment container having a gellified medium, which comprises:

a) cultivating aseptically transformed dicotyledon root organs, capable of autonomous growth in vitro, in a first compartment containing a mineral minimal medium with sugar, wherein said medium is suitable for root growth;

b) inoculating said transformed root organs with endomycorrhizal fungal spores selected from the group consisting of *Glomus intraradices, Glomus aggregatum, Glomus versiforme, Scutellospora heterogama, Glomus etunicatum, Glomus mosseae, Glomus lamellosum, Glomus macrocarpum, Gigaspora margarita,* and *Sclerocystis sp.*;

c) cultivating said inoculated transformed root organs for a time sufficient for the endomycorrhizal fungi to grow into a second root-free and root exudate-free compartment containing a mineral minimal medium without sugar and for production of endomycorrhizal fungal spores to occur in said second compartment; and d) recovering said produced endomycorrhizal fungal spores of step c) from said second root-free compartment gellified medium.

2. The method according to claim 1, wherein said transformed root organs are transformed with a bacterium containing a root-inducing plasmid or a tumor-inducing plasmid.

3. The method according to claim 1, wherein said transformed root organs are dicotyledon root organs attached to a hypocotyl to form root-hypocotyl explants.

4. The method according to claim 1, wherein said minimal medium of at least one of said first compartment and said second root-free and root exudate-free compartment further comprises a $CO_2$ source.

5. The method according to claim 1, wherein said minimal medium of said second root-free and root exudate-free compartment further comprises a $CO_2$ source.

6. The method according to claim 1, wherein said sugar is selected from the group consisting of fructose, glucose and sucrose.

7. The method according to claim 6, wherein said sugar is 1% sucrose.

8. The method according to claim 1, wherein said dicotyledon root organs are selected from the group consisting of *Daucus carota, Datura stramonium, Lycopersicon esculentum, Lycopersicon pimpinellifolium, Medicago sativa, Physalis exocorpa, Solanum melanocerasum, Tagetes patula, Tagetes erecta* and *Trifolium pratense*.

9. The method according to claim 1, wherein said gellified medium is agar or gellan.

10. The method according to claim 1, wherein said mineral minimal medium comprises $MgSO_4.7H_2O$, $KNO_3$, $KCl$, $KH_2PO_4$, $Ca(NO)_2.4H_2O$, sucrose, NaFeAEDTA, KI, $MnCl_2.4H_2O$, $ZnSO_4.7H_2O$, $H_3BO_3$, $CuSO_4.5H_2O$, $Na_2MO_4.2H_2O$, glycine, thyamine hydrochloride, pyridonine hydrochloride, nicotinic acid, and myo inositol.

11. The method according to claim 1, wherein said produced spores of step c) are recovered in step d) by liquefying said gellified medium of said second root-free and root exudate-free compartment of step c) and fitering the liquefied gellan.

12. A method of producing endomycorrhizal fungal spores in vitro in a compartmentalized bioreactor having a plurality of root-free and root exudate-free compartments having a gellified medium for endomycorrhizal fungi growth, which comprises the steps of:

a) cultivating aseptically transformed dicotyledon root organs, capable of autonomous growth in vitro, in a compartmentalized bioreactor having a plurality of first and second solid support elements, said first solid support elements defining root compartments comprising a mineral minimal medium with sugar, wherein said medium is suitable for root growth, said second solid support elements defining fungal compartments comprising a mineral minimal medium without sugar, said root compartments and said fungal compartments not being in physical contact with each other such that said fungal compartments are root-free and root exudate-free gellified compartments for endomycorrhizal fungi growth and sporulation, b) inoculating said transformed root organs of step a) with endomycorrhizal fungal spores selected from the group consisting of *Glomus intraradices, Glomus aggregatum, Glomus versiforme, Scutellospora heterogama, Glomus etunicatum, Glomus mosseae, Glomus lamellosum, Glomus macrocarpum, Gigaspora margarita,* and *Sclerocystic sp.*;

c) cultivating said inoculated transformed root organs of step b) for a time sufficient for the endomycorrhizal fungi to grow into said fungal compartments for the production of endomycorrhizal fungal spores to occur in said fungal compartments; and d) recovering said produced endomycorrhizal fungal spores of step c) from said fungal compartments.

13. The method according to claim 12, wherein said solid support elements are spherical polystyrene beads.

14. The method according to claim 12, wherein said transformed root organs are transformed with a bacterium containing a root-inducing plasmid or a tumor-inducing plasmid.

15. The method according to claim 12, wherein said dicotyledon root organs are selected from the group consisting of *Daucus carota, Datura stramonium, Lycopersicon esculentum, Lycopersicon pimpinellifolium, Medicago satira, Physalis exocorpa, Solanum melanocerasum, Tagetes patula, Tagetes erecta* and *Trifolium pratense*.

16. A method according to claim 12, wherein said mineral minimal medium comprises $MgSO_4.7H_2O$, $KNO_3$, $KCl$, $KH_2PO_4$, $Ca(NO_3)_2.4H_2O$, sucrose, NaFeEDTA, KI, $MnCl_2.4H_2O$, $ZnSO_4.7H_2O$, $H_3BO_3$, $CuSO_4.5H_2O$, $Na_2MO_4.2H_2O$, glycine, thyamine hydrochloride, pyridonine hydrochloride, nicotinic acid, and myo inositol.

17. The method according to claim 12, wherein said sugar present in said mineral medium of said root compartments is selected from the group consisting of fructose, glucose and sucrose.

18. The method according to claim 12, wherein said produced spores of step c) are recovered by liquefying said gellified medium of said root-free and root exudate-free compartment of step c) and fitering the liquefied gellified medium.

* * * * *